United States Patent [19]

Gilligan

[11] Patent Number: 4,988,196

[45] Date of Patent: Jan. 29, 1991

[54] TIME DOMAIN FRAUNHOFER LINE DISCRIMINATOR

[75] Inventor: Lawrence H. Gilligan, Charlottesville, Va.

[73] Assignee: Sperry Marine Inc., Charlottesville, Va.

[21] Appl. No.: 338,696

[22] Filed: Apr. 17, 1989

[51] Int. Cl.$^5$ .................... G01N 21/64; G01J 3/18
[52] U.S. Cl. .................... 356/308; 250/458.1; 356/328; 356/318
[58] Field of Search ............... 356/308, 309, 328, 334, 356/317, 318; 250/458.1, 459.1, 461.1

[56] References Cited

U.S. PATENT DOCUMENTS

| | | | |
|---|---|---|---|
| 3,385,160 | 5/1968 | Dawson et al. | 356/308 |
| 4,697,924 | 10/1987 | Akiyama | 356/334 X |
| 4,724,326 | 2/1988 | Poultney et al. | 250/458.1 |
| 4,804,266 | 2/1989 | Barshad | 356/308 |
| 4,862,257 | 8/1989 | Ulich | 358/95 |

Primary Examiner—Vincent P. McGraw
Attorney, Agent, or Firm—Seymour Levine

[57] ABSTRACT

A scanning spectrometer scans the spread spectrum of sunlight and low level luminescence or fluorescence past a slit to provide the spectrum scanned in the time domain. An image intensifier responsive to the light energy passing through the slit is gated on when Fraunhofer lines are coincident with the slit. A photodetector responsive to the image intensifier detects the intensified total energy within each Fraunhofer line.

19 Claims, 1 Drawing Sheet

TIME DOMAIN FRAUNHOFER LINE DISCRIMINATOR

BACKGROUND OF THE INVENTION

1. Field of the Invention

The invention relates to detecting very low level emanations such as luminescence and fluorescence in the presence of sunlight.

2. Description of the Prior Art

Some biological colonies, such as phytoplankton, spontaneously emit low level luminescence, and most organic compounds generate distinctive low level fluorescence when illuminated by solar radiation. Such emanations are useful in sensing bioligical activity or the presence of specific organic compounds. The sunlight is, however, generally so bright that such low level emanations are masked thereby, rendering it impossible to detect and analyze the luminescence or fluorescence from a remote sensor in daylight without special instrumentation.

The prior art instrumentation utilized to perform observations of such low level emanations utilizes the principle of Fraunhofer line discrimination to remotely sense luminescent organisms and fluorescent organic compounds. Such instrumentation is predicated on the phenomenon that solar radiation exhibits dark lines in the spectrum thereof caused by selective absorption of radiation by the elements in the solar atmosphere. These lines are denoted as Fraunhofer lines. Within the dark Fraunhofer lines, little or no radiation from the sun arrives at the earth. Low level luminescence and fluorescence is observed in daylight by utilizing a very narrow passband filter to effect observations within the bandwidth of a Fraunhofer line. Since the Fraunhofer line discrimination instrumentation utilizes such a narrow band filter to perform the desired observation, such instruments are limited to observing only one spectral line of approximately 0.2 Angstrom units wide per sensor. Such filters inherently function only for light incident in a very narrow angular field, thus severely limiting the field of view of such remote sensors.

SUMMARY OF THE INVENTION

The entire spectrum of the light received from a scene under observation is spatially spread and the spread spectrum is scanned in the time domain. A time domain shutter or gate sensor selectively detects the low level emanations within the bandwidths of the Fraunhofer lines. Preferably, the invention utilizes a scanning spectrometer to spread and scan the spectrum and a gated image intensifier to view the scanned spectrum through a slit. The image intensifier is gated to observe the emanations within the Fraunhofer lines. The time domain gate may be operated for as many Fraunhofer lines as desired during each scan. Thus, the disadvantage of the prior art instrumentation that was limited to one Fraunhofer line per sensor is overcome. Preferably, the front end of the apparatus of the present invention is a conventional scanning spectrometer which may be configured to have a wide field of view thereby overcoming the field of view disadvantage of the prior art instrumentation.

BRIEF DESCRIPTION OF THE INVENTION

DESCRIPTION OF THE PREFERRED EMBODIMENT

Figure 1:
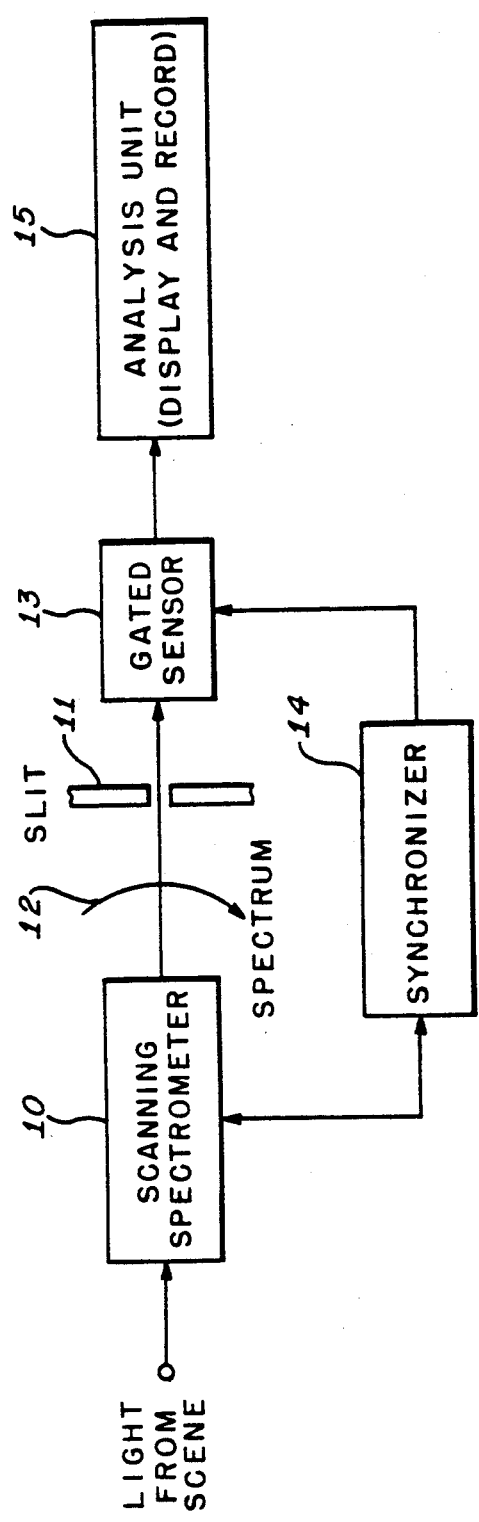
FIG. 1 is a schematic block diagram illustrating the principles of the invention.

Referring to FIG. 1, light energy from the viewed scene is received by a conventional scanning spectrometer 10. The spectrometer 10 spreads the spectrum of the received energy and cyclically moves the spread spectrum across a slit 11. The scanned spread spectrum is schematically depicted by an arrow 12. The resulting time domain spectral scan is sensed by a light sensing device 13 which may be gated on or off at the times appropriate for observing the emanations within the Fraunhofer lines. A synchronizing circuit 14 is utilized to coordinate the scanning spectrometer 10 and the sensor gate 13 so that the desired spectral lines are appropriately gated on. A conventional analysis unit 15 displays, and/or records the desired data which comprises total energy in each gated spectral line. The gated sensor 13 is preferably a present day image intensifier and the analysis unit 15 may include a photodetector, such as a photodiode, for detecting the spectral line total energy.

The apparatus of FIG. 1 provides a means of remotely sensing luminescence and fluorescence in the presence of daylight by converting the received spectrum of light to the scanned time domain signal and then gating the portions of the spectrum that lie with Fraunhofer lines. These functions are performed by the scanning spectrometer 10, the slit 11 and the gated sensor 13 which preferably comprises a gated image intensifier.

Figure 2:
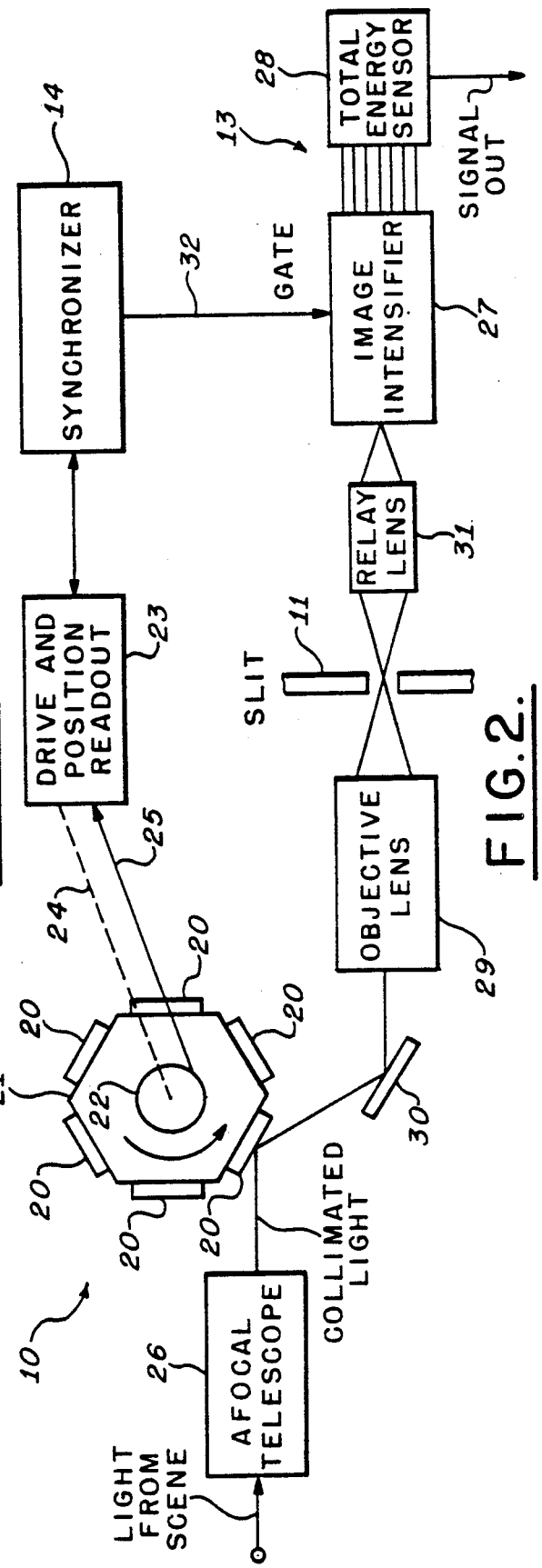
FIG. 2 is a schematic block diagram illustrating details of a preferred embodiment of the invention.

Referring to FIG. 2, in which like reference numerals indicate like components with respect to FIG. 1, details of a preferred mode of practicing the invention are depicted. FIG. 2 illustrates an optical layout of the invention and depicts a specific method of implementing the scanning spectrometer 10. A grating with an appropriate line frequency will produce a spread spectrum because of diffraction. Several gratings 20 are affixed to the facets of a rotating polygon 21 to form a rotating spectroscope. It is appreciated that the term "polygon", as used herein, comprises a shaft with a polygonal shaped cross-section. When the polygon 21 is rotated, a continuous spread spectrum is rotated in space. The polygon 21 includes an encoded disc 22 that provides a readout of the precise angular position of the polygon 21. The polygon 21 is rotated and synchronized by a conventional drive and position readout means 23. The drive 23 rotates the polygon 21 via a schematically represented coupling 24 and receives position readout from the encoded disc 22 via a line 25. It is desirable to produce each of the gratings 20 exactly alike. An economical method to manufacture the grating polygon 20, 21 is to produce the gratings 20 holographically.

An afocal telescope 26 collects energy from the scene to be analyzed. The output of the afocal telescope 26 comprises collimated light which impinges upon the facets of the grating polygon 20, 21. As discussed above, the gated sensor 13 is preferably implemented by an image intensifier 27. The output of the image intensifier 27 may be sensed by any conventional photosensor to implement the analysis unit 15 (FIG. 1). A total energy sensor 28, such as a photodiode, is illustrated.

The polygon 21 is rotated at constant speed by the drive and position readout means 23. The rotation of the polygon 21 is synchronized to an internal clock pulse source (not shown) via the synchronizer 14 and the drive and position readout means 23 receiving the precise angular position of the polygon 21 from the encoded disc 22. The rotating continuous spread spectrum is focussed upon the conventional optical slit 11 via a standard objective lens 29 and a reflecting mirror 30. Thus, the objective lens 29 focusses the energy diffracted from the grating polygon 20, 21 onto the optical slit 11 so that the light passing through the slit 11 is a time varying scanned spectrum. A conventional relay lens 31 refocusses the image of the slit upon the photocathode of the image intensifier 27, thereby relaying an amplified image of the slit onto the photodiode 28. A timing circuit within the synchronizer 14 issues a gating command to the intensifier 27, via a line 32 when desired selected Fraunhofer lines are passing the slit 11.

The present invention spreads the entire received spectrum spatially, in the manner of a diffraction grating or prism, and scans the spectrum in the time domain. The invention uses a time domain shutter or gate to sample the desired portion or portions of the spectrum. Thus, the spectrum of sunlight, including luminescent and fluorescent emanations to be detected, is scanned in time and the sensor is gated to select detection of only the desired spectral Fraunhofer lines. In effect, the apparatus of the present invention looks at the low level emanations where the sun is not shining during daylight.

While the inventon has been described in its preferred embodiment, it is to be understood that the words which have been used are words of description rather than limitation and that changes may be made within the purview of the appended claims without departing from the true scope and spirit of the invention in its broader aspects.

I claim:

1. Apparatus for detecting low level light emanations masked in sunlight, said sunlight with said emanations having a spectrum, said spectrum including at least one Fraunhofer line, comprising:
    a slit,
    spreading means for spatially spreading said spectrum of said sunlight with said emanations,
    scanning means for scanning said spread spectrum with respect to said slit,
    gated sensor means responsive to light passing through said slit from said scanned spread spectrum, and
    gating means for gating said gated sensor means when said Fraunhofer line is coincident with said slit so that said gated sensor means can sense a spectral component of said masked light emanations corresponding to said Fraunhofer line passing through said slit.

2. The apparatus of claim 1 wherein said spectrum includes a plurality of Fraunhofer lines and said gating means comprises means for gating said gated sensor means when each of said plurality of Fraunhofer lines is coincident with said slit so that said gated sensor means can sense spectral components of said masked light emanations corresponding to said Fraunhofer lines, respectively, passing through said slit.

3. The apparatus of claim 1 wherein said slit comprises an optical slit.

4. The apparatus of claim 1 wherein said spreading means and said scanning means comprises a scanning spectrometer.

5. The apparatus of claim 1 wherein said spreading means and said scanning means comprises a scanning spectrometer with a wide field of view.

6. The apparatus of claim 4 wherein said scanning spectrometer comprises
    a rotatable member with a polygonal cross-section having a plurality of faces, and
    a plurality of diffraction gratings affixed to said faces, respectively.

7. The apparatus of claim 6 wherein said scanning spectrometer further includes an afocal telescope to collimate light energy from a scene to be analyzed and to apply said collimated light energy to said rotatable polygonal member.

8. The apparatus of claim 6 wherein said scanning spectrometer further includes
    an encoder coupled to said rotatable polygonal member to provide a readout signal representative of the angular position of said member, and
    drive means coupled to said member for rotating said member at a constant speed.

9. The apparatus of claim 6 wherein said plurality of diffraction gratings are identical with respect to each other and are holographically generated.

10. The apparatus of claim 1 wherein said gated sensor means comprises
    a gated image intensifier providing an intensified output image, and
    an analysis unit coupled to receive said output image for analyzing or displaying said output image to provide spectral line output data.

11. The apparatus of claim 10 wherein said analysis unit comprises a spectral line total energy detector.

12. The apparatus of claim 11 wherein said analysis unit comprises a photodetector.

13. The apparatus of claim 12 wherein said analysis unit comprises a photodiode.

14. The apparatus of claim 10 wherein said gating means comprises synchronizing means for gating said gated image intensifier when said Fraunhofer line is coincident with said slit.

15. The apparatus of claim 8 wherein said gated sensor means comprises
    a gated image intensifier providing an intensified output image, and
    an analysis unit coupled to receive said output image for analyzing or displaying said output image to provide spectral line output data.

16. The apparatus of claim 15 wherein said gating means comprises synchronizing means for gating said gated image intensifier in accordance with said readout signal when said Fraunhofer line is coincident with said slit.

17. The apparatus of claim 1 wherein said low level light emanations comprise luminescence or fluorescence.

18. The apparatus of claim 2 wherein said gated sensor means comprises
    a gated image intensifier providing an intensified output image, and
    an analysis unit coupled to receive said output image for analyzing or displaying said output image to provide spectral line output data.

19. The apparatus of claim 18 wherein said gating means comprises synchronizing means for gating said gated image intensifier when each of said Fraunhofer lines is coincident with said slit.

* * * * *